(12) United States Patent
Komazawa et al.

(10) Patent No.: US 7,863,026 B2
(45) Date of Patent: Jan. 4, 2011

(54) MICROORGANISM HAVING AN ABILITY OF PRODUCING DOCOSAHEXAENOIC ACID AND USE THEREOF

(75) Inventors: Hiroyuki Komazawa, Asaka (JP); Masayoshi Kojima, Asaka (JP); Tsunehiro Aki, Higashi-hiroshima (JP); Kazuhisa Ono, Higashi-hiroshima (JP); Masayuki Kawakami, Asaka (JP)

(73) Assignee: FUJIFILM Corporation, Tokyo (JP)

( * ) Notice: Subject to any disclaimer, the term of this patent is extended or adjusted under 35 U.S.C. 154(b) by 751 days.

(21) Appl. No.: 11/774,261

(22) Filed: Jul. 6, 2007

(65) Prior Publication Data

US 2008/0009045 A1    Jan. 10, 2008

Related U.S. Application Data

(62) Division of application No. 10/743,832, filed on Dec. 24, 2003, now Pat. No. 7,259,006.

(30) Foreign Application Priority Data

Dec. 27, 2002  (JP) ............... 2002/378907
Sep. 9, 2003   (JP) ............... 2003/317110
Dec. 12, 2003  (JP) ............... 2003/415270

(51) Int. Cl.
*C12P 7/64* (2006.01)

(52) U.S. Cl. .................. 435/134; 435/254.1

(58) Field of Classification Search .............. None
See application file for complete search history.

(56) References Cited

U.S. PATENT DOCUMENTS 5,130,242 A  7/1992  Barclay
6,566,123 B1  5/2003  Barclay

FOREIGN PATENT DOCUMENTS

EP  0 512 997 B1  6/1997
EP  0 669 809 B1  4/2003

OTHER PUBLICATIONS

Bajpai et al. (1991), "Optimization of Production of Docosahexaenoic Acid (DHA) by Thraustochytrium Aureum ATCC 34304"; JAOCS; vol. 68, No. 7:509-514.
Bajpai et al. (1991), "Production of Docosahexaenoic Acid by Thraustochytrium Aureum"; Appl. Microbiol Biotechnol; 35:706-710.
Iida et al. (1996); "Improvement of Docosahexaenoic Acid Production in a Culture of Thraustochytrium Aureum by Medium Optimization"; Journal of Fermentation and Bioengineering; vol. 81, No. 1:76-78.
Kendrick et al. (1992); "Lipids of Selected Molds Grown for Production of n-3 and n-6 polyunsaturated fatty acids"; Lipids; 27(1):15 20 (**Abstract Only).
Lewis et al. (1999); "The Biotechnological Potential of Thraustochytrids"; Mar. Biotechnology; 1:580-587.
Li et al. (1994); "Production of Docosahexaenoic Acid by Thraustochytrium Roseum"; Journal of Industrial Microbiology; 13:238-241.
Singh et al. (1996); Docosahexaenoic Acid (DHA) Production by Thraustochytrium sp. ATCC 20892; World Journal of Microbiology and Biotechnology 12:76-81.
Singh et al. (1996); "Production of High Yields of Docosahexaenoic Acid by Thraustochytrium Roseum ATCC 28210"; Journal of Industrial Microbiology; 16:370-373.
Weete et al. (1997); "Lipids and Ultrastucture of Thraustochytrium sp. ATCC 26185"; Lipids; 32(8):839-845 (**Abstract only).
Yongmanitchai et al. (Aug. 1989); "Omega-3 Fatty Acids: Alternative Sources of Production"; Process Biochemistry; 117-125.

*Primary Examiner*—Irene Marx
(74) *Attorney, Agent, or Firm*—Sughrue Mion, PLLC

(57) ABSTRACT

An object of the present invention is to provide a microorganism which has a high ability of producing docosahexaenoic acid. The present invention provides a *Thraustochytrium* strain which has an ability of producing docosahexaenoic acid, and use thereof.

5 Claims, 3 Drawing Sheets

US 7,863,026 B2

MICROORGANISM HAVING AN ABILITY OF PRODUCING DOCOSAHEXAENOIC ACID AND USE THEREOF

This is a divisional of application Ser. No. 10/743,832 filed Dec. 24, 2003 now U.S. Pat. No. 7,259,006. The entire disclosure of the prior application, application Ser. No. 10/743,832, is hereby incorporated by reference.

TECHNICAL FIELD

The present invention relates to a novel microorganism having an ability of producing docosahexaenoic acid (DHA) and the use of said microorganism.

BACKGROUND ART

Docosahexaenoic acid is a polyunsaturated fatty acid which is present specifically in the brain or retina of an animal. It plays a major physiological role in those organs, and also has physiological activities such as an anti-inflammatory effect or an effect of lowering blood cholesterol level. Accordingly, docosahexaenoic acid is a useful substance, the use of which has drawn attention in the fields of medicines and food products. Recently, use of docosahexaenoic acid has also been expanded in the field of functional foods such as health foods and formulas.

Docosahexaenoic acid is contained in fish oil of bluefish. More particularly, about 20% of sardine- or tuna-derived oil is made up of docosahexaenoic acid. A major problem in terms of the use of fish-derived docosahexaenoic acid-containing fat and oil in the field of food products is necessity of considerable operations for removing the smell of fish. Furthermore, since fish-derived docosahexaenoic acid-containing fat and oil contains a variety of polyunsaturated fatty acids such as arachidonic acid or icosapentaenoic acid (EPA), it is likely to be oxidized. Thus, it is difficult to obtain fat and oil having stable quality. Further, when docosahexaenoic acid is used in the field of medicines or the like, it is necessary that docosahexaenoic acid is separated and purified from docosahexaenoic acid-containing fat and oil. However, a variety of polyunsaturated fatty acids having structures similar to that of docosahexaenoic acid are contained, and thus, separation and purification are difficult. In the preparation of formulas, docosahexaenoic acid-containing fat and oil having a low content of icosapentaenoic acid is particularly preferable. However, when the source is fish oil, it is very difficult to efficiently remove icosapentaenoic acid only.

As a source of docosahexaenoic acid other than fish oil, a method for producing docosahexaenoic acid using microorganisms have been attempted. Examples of known microorganisms which produce docosahexaenoic acid-containing fat and oil include *Vibrio marinus* (bacteria extracted from the deep sea); *Vibrio* (bacteria separated from the intestine of deep-sea fish); *Thraustochytrium aureum* which is *Mastigomycotina; Japonochytrium* sp.; and *Cyclotella cryptica*, which is a type of microalgae. Production of docosahexaenoic acid-containing fat and oil by culture techniques utilizing these microorganisms have also been studied (JP Patent Publication (Kokai) No. 1-199588 A (1989)). However, according to the conventionally known methods utilizing microorganisms, the production amount of docosahexaenoic acid-containing fat and oil per liter of medium was as small as approximately 100 mg to 700 mg, and the production amount of docosahexaenoic acid was also very small.

JP Patent Publication (Kokai) No. 10-72590 A (1998) and JP Patent No. 2764572 disclose the production of docosahexaenoic acid using the *Schizochytrium* sp. strain (SR21). In these documents, drawbacks such as small production amounts, necessity of a special medium for culturing, and necessity of new capital investment for equipment for production are also pointed out.

JP Patent Publication (Kohyo) No. 2000-513575 discloses that fat and oil can be collected from cultured microorganisms of the genus *Ulkenia* that has an ability of producing docosahexaenoic acid- and docosapentaenoic acid-containing fats and oils, but there are same drawbacks as mentioned above.

Rapeseed oil is often used as a starting material for long-chain saturated fatty acid (C22:0 behenic acid) which is necessary for photographic photosensitive materials. A rapeseed breed containing no C22 component has become preferred, and the breed improvement thereof has been in progress. Thus, the supply of a rapeseed breed containing C22 component tends to decrease. In addition, hydrogenated rapeseed oils contain fatty acid having similar numbers of carbon atoms, and thus, laborious purification and cost are of serious problem for the production of highly purified behenic acid. Therefore, it is desired to develop a technique for producing useful lipids, which can stably provide highly purified DHA and behenic acid at a low cost.

DISCLOSURE OF THE INVENTION

An object of the present invention is to provide a microorganism which has a high ability of producing docosahexaenoic acid. It is another object of the present invention to provide a method for very efficiently producing docosahexaenoic acid-containing fat and oil at high yield without complicated processes by utilizing a microorganism which has an ability of producing docosahexaenoic acid. It is further another object of the present invention to provide a method for efficiently producing docosahexaenoic acid.

The present inventors have conducted concentrated studies in order to attain the above objects. As a result, they have found a microorganism (strain) which produces highly purified docosahexaenoic acid (DHA). This microorganism can be easily cultured, and can produce fat and oil which contain a large amount of DHA. A highly purified DHA can be easily collected from such fat and oil. By hydrogenating and hydrolyzing the unsaturated fatty acid (C22) component of fat and oil which is produced from this organism, highly purified behenic acid can be obtained. The present invention has been completed based on these findings.

Thus, the present invention provides a *Thraustochytrium* strain which has an ability of producing docosahexaenoic acid.

Preferably, the LFF1 strain of *Thraustochytrium* (accession number: FERM BP-08568 (transferred from FERM P-19159)), a strain of the same genus as the LFF1 strain, and a strain having fungological properties substantially identical to those of the LFF1 strain, are provided.

Another aspect of the present invention provides a method for producing docosahexaenoic acid-containing fat and oil, which comprises culturing the *Thraustochytrium* strain having an ability of producing docosahexaenoic acid in a medium, and collecting the docosahexaenoic acid-containing fat and oil from the culture product.

Preferably, the *Thraustochytrium* strain having an ability of producing docosahexaenoic acid is the LFF1 strain of *Thraustochytrium* (accession number: FERM BP-08568 (transferred from FERM P-19159)), a strain of the same genus as the LFF1 strain, or a strain having fungological properties substantially identical to those of the LFF1 strain.

Preferably, pH at culturing is 8.0 to 9.0. Preferably, the amount of strain to be inoculated at culturing is 80 g or more, more preferably 100 g or more, per liter of culture medium. Preferably, the strain is cultured in a medium having a carbon source concentration of 4% to 7%, and then is subsequently cultured in a medium having a carbon source concentration of 13% to 20%.

A further aspect of the present invention provides docosahexaenoic acid-containing fat and oil which contains 10% by weight or less of docosapentaenoic acid and 30% by weight or more of docosahexaenoic acid, based on the total amount of fatty acid in the fat and oil. Preferably, there is provided docosahexaenoic acid-containing fat and oil which contains 10% by weight or less of docosapentaenoic acid, 30% by weight or more of docosahexaenoic acid, and 4% by weight or less of icosapentaenoic acid.

Preferably, the fat and oil according to the present invention contains 50% by weight or more of docosahexaenoic acid, based on the total amount of fatty acid in the fat and oil.

Preferably, the fat and oil according to the present invention is obtained by culturing the *Thraustochytrium* strain having an ability of producing docosahexaenoic acid in a medium and collecting docosahexaenoic acid-containing fat and oil from the culture product.

Preferably, the fat and oil according to the present invention is obtained by culturing the LFF1 strain of *Thraustochytrium* (accession number: FERM BP-08568 (transferred from FERM P-19159)), a strain of the same genus as the LFF1 strain, or a strain having fungological properties substantially identical to those of the LFF1 strain in a medium and collecting docosahexaenoic acid-containing fat and oil from the culture product.

Preferably, the fat and oil according to the present invention is obtained by purifying fat and oil which is collected from the cultured product of a strain.

Preferably, the fat and oil according to the present invention is contained in: a culture solution during the production of fat and oil by culturing of strain or a sterilized culture solution thereof; a culture solution after the completion of culture or a sterilized culture solution thereof; cultured strains collected from any of the above culture solutions or a dehydrated product thereof; or a residue after the fat and oil is collected from any of the above culture solutions or strains.

A further aspect of the present invention provides a method for producing docosahexaenoic acid, which comprises isolating docosahexaenoic acid from the docosahexaenoic acid-containing fat and oil which is obtained by the production method according to the present invention. Preferably, the docosahexaenoic acid is isolated, after the docosahexaenoic acid-containing fat and oil is treated with lipase.

A further aspect of the present invention provides a method for producing behenic acid, which comprises performing hydrogenation on the aforementioned docosahexaenoic acid-containing fat and oil or docosahexaenoic acid.

A further aspect of the present invention provides a method for producing photographic photosensitive materials, wherein silver behenate containing the aforementioned behenic acid is used.

DETAILED DESCRIPTION OF THE INVENTION

Figure 1:
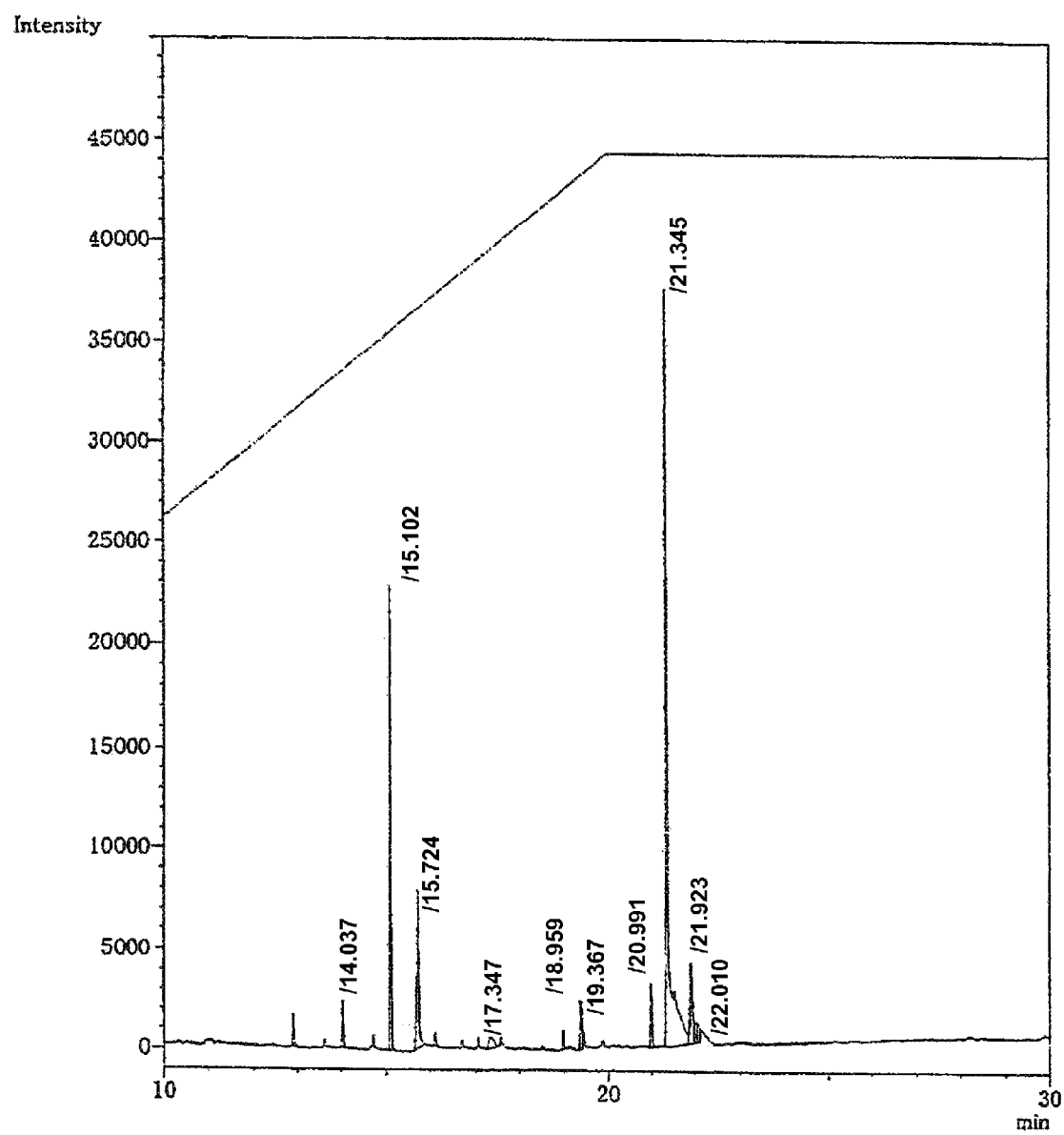
FIG. 1 shows the result of gas chromatography analysis of the lipid composition of the fat and oil which were produced by using the LFF1 strain of the genus *Thraustochytrium*.

The embodiments of the present invention are hereafter described in detail.

(1) A Strain of the Present Invention

Any *Thraustochytrium* strain which has an ability of producing docosahexaenoic acid can be used as the strain of the present invention. Such strain preferably contains 10% by weight or less of docosapentaenoic acid and 30% by weight or more of docosahexaenoic acid, based on the total amount of fatty acid in fat and oil contained in the cultured produce of a strain.

The strain of the present invention can be selected by, for example, a screening technique as described below. First, collected seawater is subjected to filtration using a 0.4-μm sterilized filter, and bacteria is collected. This filter is then attached to an agar medium comprising 90% natural seawater, glucose, yeast extract, and peptone, followed by culturing at 20 to 30° C. A colony formed on the filter of this agar plate medium is cultured on an agar medium having the same composition as the above medium, the obtained strains are collected using a spatula. Fatty acid is directly methyl-esterified from the strains by a conventional technique, the composition thereof is analyzed by gas chromatography, and a strain that produces docosahexaenoic acid is selected. Further, a strain that accumulates 10% by weight or more, and preferably 20% by weight or more of fat and oil, based on a dried strain, and/or 10% by weight or less of docosapentaenoic acid and 30% by weight or more of docosahexaenoic acid, based on the total amount of fatty acid in fat and oil, can be selected.

Examples of the strain of the present invention include the LFF1 strain of *Thraustochytrium* (accession number: FERM BP-08568 (transferred from FERM P-19159)), a strain of the same genus as the LFF1 strain, and a strain having fungological properties substantially identical to those of the LFF1 strain.

The LFF1 strain of the genus *Thraustochytrium* was collected from the Seto Inland Sea. The ectoplasmic net of the LFF1 strain extending from spherical cells with diameters of 10 μm to 20 μm can be observed in an adequate agar medium (for example, 2% agar medium comprising 3% glucose, 0.5% yeast extract, 0.5% peptone, and 2% synthetic seawater). This strain was recognized to belong to the kingdom Chromista, the class Labyrinthulea, the family Thraustochytriaceae. The nutritive cells did not exhibit any motility, and they were converted to the polynuclear state through repetition of nuclear divisions not involving cytoplasmic division. Thereafter, they formed zoospores, and these zoospores were extracellularly discharged. Such a life history is characteristic of the genera *Thraustochytrim* (Olive, L. S., The Mycetozoans, Academic Press, New York, U.S.A., 1975; Daisuke Honda, "*Rabirinchura-rui no keito to bunrui* (Phylogeny and taxonomy of the Labyrinthula)"; *Kaiyo to seibutu* (Aquabiology), vol. 23: pp. 7-18, 2001).

This classification is apparent because significant amounts of docosahexaenoic acid and docosapentaenoic acid, which are characteristics of the family Thraustochytriaceae, are contained in the intracellular lipid of the LFF1 strain, and the LFF1 strain falls in the cluster of the genus *Thraustochytrium* based on the molecular systematic analysis of the nucleotide sequence of 18S rRNA. Regarding the classification of the family Thraustochytriaceae, however, the classification system based on the morphology or life-history is inconsistent with the molecular systematic classification (Honda, D. et al., Molecular phylogeny of Labyrinthulids and Thraustochytrids based on the sequencing of 18S ribosomal RNA gene, Journal of Eukaryotic Microbiology 46: 637-647, 1999). Therefore, the species of the LFF1 strain has not yet been identified.

The LFF1 strain of the genus *Thraustochytrium* of the present invention was deposited as of Dec. 17, 2002, at the International Patent Organism Depositary of the National Institute of Advanced Industrial Science and Technology (IPOD) (Tsukuba Central 6, 1-1-1 Higashi, Tsukuba, Ibaraki, Japan) under the accession number FERM P-19159. FERM P-19159 was transferred to an international deposit under the accession number FERM BP-08568 on Dec. 10, 2003. The complete taxonomic description of the deposited microorganism is as follows: Chromista, Labyrinthulales, Thraustochytriaceae, *Thraustochytrium*. The deposited material has been accepted for deposit under the Budapest Treaty on the International Recognition of the Deposit of Microorganisms for the purpose of Patent Procedure. All restrictions on the availability to the public of the material so deposited will be irrevocably removed upon the granting of a patent.

The strain of the present invention is not limited to the aforementioned LFF1 strain of the genus *Thraustochytrium* (accession number: FERM BP-08568 (transferred from FERM P-19159)), and includes a strain of the same genus as the LFF1 strain, and a strain having fungological properties substantially identical to those of the LFF1 strain.

As mentioned herein above, the strain of the same genus as the LFF1 strain and a strain having fungological properties substantially identical to those of the LFF1 strain can be identified by observing properties (for example, the ectoplasmic net extending from spherical cells with diameters of 10 μm to 20 μm) in an adequate agar medium (for example, 2% agar medium comprising 3% glucose, 0.5% yeast extract, 0.5% peptone, and 2% synthetic seawater) or observing the properties of nutritive cells (for example, lack of motility, conversion to a polynuclear state through repetition of nuclear divisions not involving cytoplasmic division, and thereafter formation of zoospores and extracellular discharge of the zoospores).

A variant or recombinant of the LFF1 strain, the strain of the same genus as the LFF1 strain, or a strain having fungological properties substantially identical to those of the LFF1 strain as mentioned above, is also within the scope of the present invention.

For example, all variants and recombinants which were designed to produce a large amount of docosahexaenoic acid are within the scope of the present invention. Such variants or recombinants are those that are designed to contain a larger amount of docosahexaenoic acid in fat and oil as compared with the amount produced by the wild type, those that are designed to have a larger amount of total fat and oil as compared with the amount produced by the wild type, or those that are designed to satisfy both conditions. Further, a strain that was designed to produce fat and oil containing the same amount of docosahexaenoic acid as the corresponding wild type by efficiently using a substrate having excellent cost-effectiveness, is also within the scope of the present invention.

(2) Production of Docosahexaenoic Acid-Containing Fat and Oil

Docosahexaenoic acid-containing fat and oil can be produced by culturing the *Thraustochytrium* strain having an ability of producing docosahexaenoic acid according to the present invention in a medium and collecting docosahexaenoic acid-containing fat and oil from the culture product.

The *Thraustochytrium* strain (e.g., the LFF1 strain) can be proliferated by inoculating it in an adequate medium prepared from natural seawater or synthetic seawater, followed by culturing by a conventional technique. The amount of seed strain to be inoculated in culture medium is not particularly limited, and is preferably 80 g or more per liter of culture medium, more preferably 100 g or more per liter of culture medium. By performing culturing under such condition, the production amount of fat and oil can be increased.

Any conventional medium can be used as a medium. Examples of carbon sources include carbohydrates such as glucose, fructose, saccharose, and starch, as well as fats and oils such as oleic acid or soybean oil, glycerol, and sodium acetate. These carbon sources can be used in amounts of, for example, 20 to 300 g per liter of medium. In a particularly preferred embodiment, culturing can be performed by using two types of medium, each of which has a different concentration of carbon source with each other. For example, a strain is cultured in a medium having a carbon source concentration of 4% to 7%, and then is subsequently cultured in a medium having a carbon source concentration of 13% to 20%. By performing culturing under such condition, the production amount of fat and oil can be increased.

Examples of nitrogen sources that can be used include organic nitrogen such as yeast extract, corn steep liquor, polypeptone, sodium glutamate, and urea, and inorganic nitrogen such as ammonium acetate, ammonium sulfate, ammonium chloride, sodium nitrate, and ammonium nitrate. Potassium phosphate and the like can be suitably combined and used as inorganic salts.

In order to promote the production of docosahexaenoic acid, a docosahexaenoic acid precursor can be added to a medium. Examples of a precursor include, but are not limited to, hydrocarbons such as tetradecane, hexadecane, and octadecane, fatty acids such as tetradecanoic acid, hexadecanoic acid, octadecanoic acid, and oleic acid, salts thereof (e.g., sodium salt or potassium salt), fatty acid ester, and fats and oils comprising fatty acid as a constituent (e.g., olive oil, soybean oil, cottonseed oil, and palm oil).

Preferably, the aforementioned medium is adjusted to a pH level between 4.0 and 9.5 with the addition of adequate acid or base after its preparation, and is then sterilized in an autoclave.

The culture temperature for the strain is generally between 10° C. and 45° C., and preferably between 20° C. and 37° C. The culture temperature is preferably controlled in such a way that the fat and oil composition of interest can be produced. The pH level of the culture is generally between 3.5 and 9.5, and preferably between 4.5 and 9.5. A particularly preferred pH level is different depending on the purpose. pH 5.0 to 8.0 is preferred for producing a large amount of fat and oil. The present inventors have found that the production amount of fat and oil is decreased but the content of docosahexaenoic acid in fat and oil is increased by adjusting pH to 8.0 to 9.0.

The culture period can be set between, for example, 3 to 7 days, and culture can be carried out by aeration agitation culture, shaking culture, or standing culture.

Thus, a strain which accumulates docosahexaenoic acid-containing fat and oil at a high concentration in its culture product is generally produced at a high concentration level of about 4 g to 60 g based on the weight of dried strain per liter of medium. A culture solution and a strain can be separated from the culture product by a technique known to persons skilled in the art, such as centrifugation or filtration. Centrifugation is particularly preferable.

The strain separated from the above culture product is fractured by, for example, ultrasonic or Dynomill, and then extracted with a solvent such as chloroform, hexane, or butanol. Thus, docosahexaenoic acid-containing fat and oil can be obtained.

The content of docosahexaenoic acid-containing fat and oil per 100 g of dried strain is about 10 g to 80 g, and the production amount of docosahexaenoic acid-containing fat and oil per liter of medium is about 0.4 g to 48 g.

In a preferable embodiment of the present invention, the content of docosahexaenoic acid in fatty acid components of fat and oil is as high as 50% by weight or more. Accordingly, the production amount of docosahexaenoic acid per liter of medium is very high at about 0.2 g to 38 g.

The *Thraustochytrium* strain having an ability of producing the docosahexaenoic acid according to the present invention can preferably accumulate 10% by weight or more and more preferably 20% by weight or more of fat and oil, based on the dried strain. Fat and oil which are produced by using the strain of the present invention are docosahexaenoic acid-containing fat and oil containing 10% by weight or less of docosapentaenoic acid and 30% by weight or more of docosahexaenoic acid, and preferably 4% by weight or less of icosapentaenoic acid, based on the total amount of fatty acids. Such docosahexaenoic acid-containing fat and oil preferably contain 50% by weight or more of docosahexaenoic acid based on the total amount of fatty acids.

(3) Production of Docosahexaenoic Acid

Docosahexaenoic acid can be separated from docosahexaenoic acid-containing fat and oil in a state of mixed fatty acids or fatty acid ester by concentrating and collecting it by means of conventional techniques, such as urea addition, separation by cooling, high-performance liquid chromatography, or supercritical chromatography.

Also, fat and oil containing a high amount of docosahexaenoic acid can be produced by releasing and removing fatty acids having a short length of strand from docosahexaenoic acid-containing fat and oil. This reaction can be carried out by using various hydrolases such as esterase or lipase. Treatment with lipase is particularly preferred, and treatment with 1,3-positions selective lipase is more preferred.

Many types of lipase derived from animals, plants or microorganisms have been reported. Castor lipase, a plant derived lipase, is known to have a low position-selectivity. Examples of lipases of microorganisms having a low position-selectivity include *Candida cylindracea, Chromobacterium viscosum, Corynebacterium acnes, Geotrichum candium, Pseudomonas fragi, Pseudomanas fluorescens*, and *Penicillium cyclopium*. Examples of lipases of microorganisms having a 1,3-position selectivity include *Rhizopus delemar, Rhizopus arrhizus, Rhizopus niveus, Mucor miehei, Aspergillus niger, Rhizopus oryzae*, and *Penicillum roqueforti*. The activity of pancreatic lipase derived from animals is well known to be an example of 1,3-position selective lipases. Examples of 1,3-position selective lipases which can be industrially produced and can be safely used at low cost include 1,3-position selective lipases derived from the aforementioned microorganisms and a lipase derived from pig pancreas, and particularly preferred examples include those derived from *Rhizopus oryzae, Aspergillus niger* or *Penicillum roqueforti*.

The reaction of lipase treatment can be carried out at pH 4.0 to 9.0 at 20° C. to 60° C.

When the *Thraustochytrium* strain (e.g., the LFF1 strain) is used as a strain, a fatty acid component of the docosahexaenoic acid-containing fat and oil which are obtained is 10% by weight or less of docosapentaenoic acid and 30% by weight or more of docosahexaenoic acid (further preferably 50% by weight or more), and preferably 4% by weight or less of icosapentaenoic acid, based on the total amount of fatty acid. Such fat and oil is advantageous for concentration and separation of docosahexaenoic acid. The aforementioned fat and oil contains substantially no fatty acid having physiological activities similar or agonistic to that of docosahexaenoic acid. Thus, application thereof is convenient in the fields of functional foods or medicines, and utilization thereof is particularly convenient in the production of behenic acid which is used for photographic photosensitive materials.

(4) Utilization of Fat and Oil and Docosahexaenoic Acid

The fat and oil and the docosahexaenoic acids described in (2) and (3) above can be added to various foods and drinks, feeds or bait. Examples of such foods include nutritional supplementary foods, modified milk for infants or premature babies, health foods, functional foods, baby foods, food for pregnant women, and foods for elderly people. Feeds include livestock feeds for pigs or cows, poultry feeds for chickens, pet foods for dogs or cats, and feed for pisciculture. Examples of bait include feeds for microorganisms (so-called animal plankton) that is provided as bait for the aquafarming of seafood. The use of the cultured product of the strain of the present invention, a strain collected from the aforementioned culture product, or a residue of the strain after fat and oil have been removed therefrom for feeds and bait are particularly preferable from the economical point of view.

When the fat and oil and the docosahexaenoic acids produced by the method of the present invention are added to foods and drinks, the composition of the foods and drinks may be in a solid, liquid, or fat-and-oil-containing form. The contents of fat and oil and docosahexaenoic acid in foods and drinks depend on properties of foods and drinks, and the content is preferably about 0.001% by weight to 50% by weight.

Examples of fat and oil-containing foods include: natural foods containing fat and oil such as meat, fish, or nuts; foods to which fat and oil is added when preparing, such as soups and the like; foods using fat and oil as a heat medium, such as doughnuts and the like; fat and oil foods such as butter; processed foods to which fat and oil is added during processing, such as cookies or the like; and foods to which fat and oil is sprayed or upon which it is coated when finishing processing, such as hard biscuits and the like. The fat and oil (or the separated docosahexaenoic acid) of the present invention may also be added to fat-and-oil-free agricultural foods, fermented foods, livestock food products, aquatic foods, or drinks.

The fat and oil and the docosahexaenoic acid of the present invention may be added to functional foods. Functional foods may be in the form of medical preparations or in processed forms such as enteral feeding products, powders, granules, troches, liquid medications, suspensions, liquid emulsions, or syrups, which comprise a protein, saccharide, lipid, trace element, vitamins, emulsifier, or aromatic in combination with the fat and oil of the present invention.

Further, the fat and oil and the docosahexaenoic acid of the present invention can be used as additives for cosmetics or washing agents or as starting materials for producing its derivative used for medicines.

Forms of cosmetics are not particularly limited, and examples thereof include emulsions, creams, lotions, masks, dispersion liquids, and washing agents. Bases for cosmetics can be selected in accordance with the forms of cosmetics. Examples thereof that can be used include purified water, lower alcohols, polyhydric alcohols, fats and oils, surfactants, various cosmetic ingredients, ultraviolet absorbers, thickeners, pigments, antiseptics, and aromatics. Washing agents include soaps, shampoos, facial creams, and conditioners that are commonly used to keep bodies clean, regardless of whether they are medicinal or nonmedicinal. Further, they may be bath agents, or detergents for equipment usually used at home, such as plates and utensils.

The fat and oil and the docosahexaenoic acid of the present invention are particularly useful as starting materials for silver behenate, which is a component of photographic photosensitive materials. This is described below.

(5) Production of Behenic Acid and Production of Photographic Photosensitive Materials Using Behenic Acid Behenic acid can be produced by hydrogenating the docosahexaenoic acid-containing fat and oil or docosahexaenoic acid as mentioned herein above. When fat and oil is used as a starting material, behenic acid can be produced by performing hydrolysis after the hydrogenation.

The behenic acid which is produced by the method of the present invention can be used for producing silver behenate used as a component of photographic photosensitive materials. Specifically, a method for producing photographic photosensitive materials by using silver behenate which contains the behenic acid produced by the method of the present invention is also within the scope of the present invention.

Specific techniques for producing the photographic photosensitive materials are known to persons skilled in the art, and are described in, for example, JP Patent Publication (Kokai) Nos. 2002-341484 A, 2002-328444 A, 2002-318431 A, 2002-311533 A, or 2002-311531 A.

The present invention is described in more detail with reference to the following examples, although the scope of the present invention is not limited to these examples.

EXAMPLES

Example 1

Isolation and Identification of the LFF1 Strain

The LFF1 strain was collected from the Seto Inland Sea. The ectoplasmic net of the LFF1 strain extending from spherical cells with diameters of 10 μm to 20 μm can be observed in an adequate agar medium (2% agar medium comprising 3% glucose, 0.5% yeast extract, 0.5% peptone, and 2% synthetic seawater). This strain was recognized to belong to the kingdom Chromista, the class Labyrinthulea, and the family Thraustochytriaceae. The nutritive cells did not exhibit any motility, and they were converted to a polynuclear state through repetition of nuclear divisions not involving cytoplasmic division. Thereafter, they formed zoospores, and these zoospores were extracellularly discharged. Such a life history is characteristic of the genera *Thraustochytrim* (Olive, L. S., The Mycetozoans, Academic Press, New York, U.S.A., 1975; Daisuke Honda, "*Rabirin-chura-rui no keito to bunrui* (Phylogeny and taxonomy of the Labyrinthula)", *Kaiyo to seibutu* (Aquabiology), vol. 23: pp. 7-18, 2001).

Example 2

Production of Fat and Oil Using the LFF1 Strain

The LFF1 strain was cultured using a jar fermenter under the following conditions to produce fat and oil. The composition of the produced fat and oil was analyzed by gas chromatography.

(1) Culture Conditions:
   use of a 3-liter fermenter;
   amount of culture: 1.8 liters of culture; and
   composition of medium:
   10% glucose;
   3.3% yeast extract;
   50% synthetic seawater;
   0.1% defoaming agent;
   0.2% ammonium acetate; and
   0.2% monobasic potassium phosphate.

The LFF1 strain for subculture was streaked onto agarose medium and then subjected to standing culture at 28° C. for 4 days. The appeared colonies were then refrigerated.
   Agarose medium:
   3% glucose;
   1% yeast extract;
   50% synthetic seawater;
   0.2% ammonium acetate;
   0.2% monobasic potassium phosphate; and
   1.5% agarose The aforementioned colonies were collected and then subjected to preculture while stirring in 80 ml of medium at 28° C. under aerobic conditions for 16 hours. A fermenter was inoculated with the culture product. Agitation culture was conducted for 40 hours with aeration at 500 rpm. pH was not regulated. After the strains were collected at 1,500 G for 30 minutes, the wet weight was measured. After being frozen at −40° C., lyophilization was carried out overnight, and the dry weight was measured.

Conditions for Disruption and Extraction

Strains were extracted by adding a mixture of chloroform and methanol with a chloroform-to-methanol ratio of 2:1 in an amount 10 times greater than that of the strain (based on a wet weight) and also adding glass beads in an amount equivalent to that of the strain (based on a wet weight), and then stirring the resultant mixture under water cooling in a high-performance agitator. The disrupted strains were separated by filtration, extracted and washed twice with an equivalent amount of saturated saline solution, and then dried over sodium sulfate. The solvent was removed using an evaporator, and the weight of roughly purified oil was measured.

Preparation of Samples For Gas Chromatography

The oil was dissolved with the aid of chloroform, a mixture of 10% KOH (aq) and ethanol in equal proportions was added, and the mixture was hydrolyzed at 95° C. for 2 hours. The product was neutralized with 2N HCl and then extracted with ether. TMS diazomethane was added thereto, the mixture was subjected to esterification at room temperature for 2 hours, and acetic acid was finally added thereto to terminate the reaction. This reaction solution was analyzed by gas chromatography. A chart for gas chromatography is shown in FIG. 1.

Conditions For Gas Chromatography
  Column: DB-17 (0.25 mm×30 m)
  Carrier gas: He inlet pressure of 250 kPa
  Column temperature: 100° C. to 250° C. (rate of temperature increase: 10° C./minute)
  Detection: FID
  The results of culture are shown below.
  Culture period: 40 hours
  Weight of dried strains: 24.0 g/liter of culture
  Total amount of fat and oil: 5.95 g/liter of culture
  Fat and oil content: 24.8% (total fat and oil/weight of dried strains)
  Amount of DHA: 3.50 g/liter of culture
  C22 lipid: 3.69 g/liter of culture

| Lipid composition | |
| --- | --- |
| C15:0 | 1.8% |
| C16:0 | 18.8% |
| C17:0 | 9.7% |
| C20.5 (EPA) | 2.2% |
| C22:5 (DPA) | 3.2% |
| C22:6 (DHA) | 58.8% |

Example 3

Conversion to Behenic Acid

The Labyrinthula oil extract (10 g), which is the total fat and oil produced and extracted in Example 2, was allowed to react in the presence of 0.05 g of stabilized Ni catalyst in 100 ml of ethanol in an autoclave at 150° C. and 2 Mpa for 5 hours. After the reaction, the temperature of the reaction product was cooled to room temperature, and 100 ml of chloroform was added to dissolve the product. Thereafter, the Ni catalyst was removed from this solution by celite filtration, and the solvent was removed by distillation under reduced pressure.

An aqueous solution of 10% potassium hydroxide (25 ml) and ethanol (50 ml) were added to the hydrogenation product, and the mixture was subjected to reflux while stirring for 30 minutes. After the product was cooled to room temperature, the generated crystal was filtered and then washed with 20 ml of ethanol.

The obtained crystal was added to 50 ml of water and ethanol mixed in equal proportions, 10 ml of 10% hydrochloric acid was added thereto, and the mixture was stirred at room temperature for 1 hour. The generated crystal was filtrated and then washed with 20 ml of ethanol. By allowing this hydrolysate to be distilled (0.5 mm Hg, 185° C.), 5 g of behenic acid (purity: 95%) could be obtained.

Example 4

Figure 2:
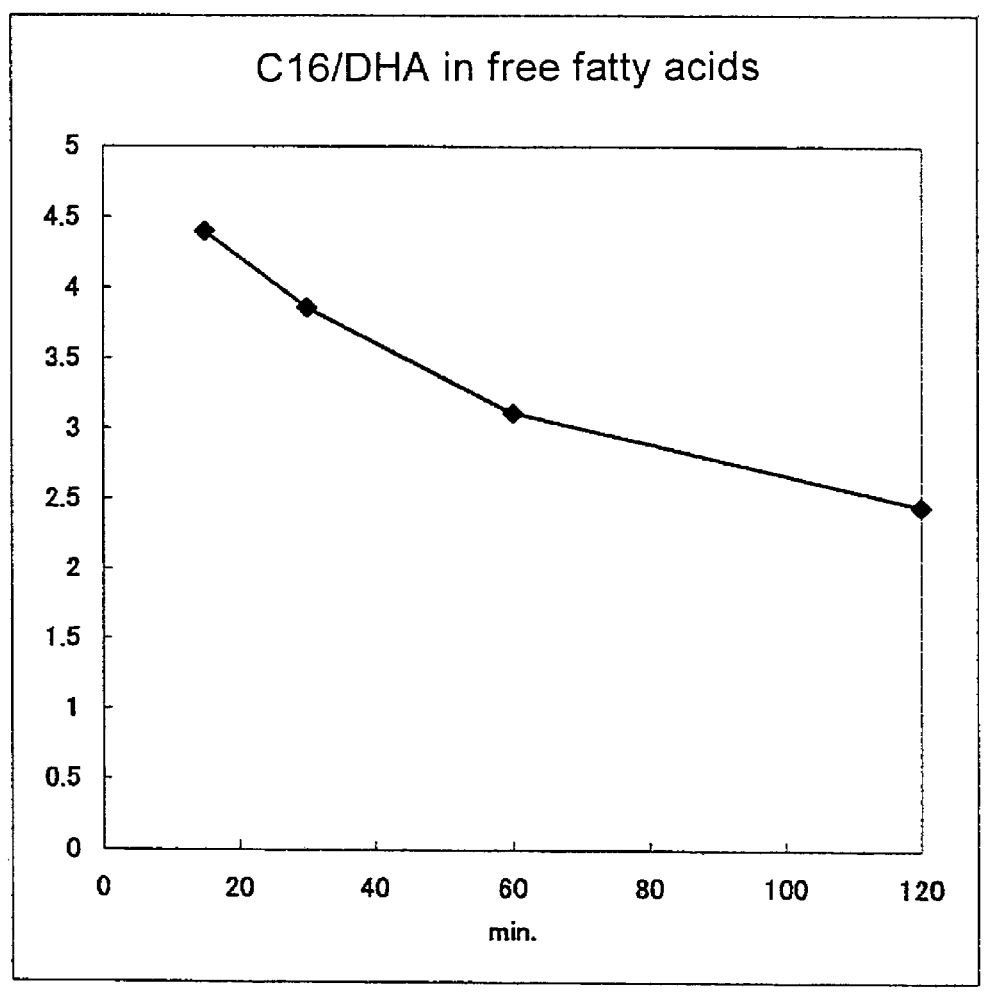
FIG. 2 shows the result of hydrolysis of fat and oil produced by LFF1 strain by means of lipase of Amano (F-AP15) as a ratio of palmitic acid and docosahexaenoic acid in free fatty acids.

To 0.2 g of the lipid which was extracted from the LFF1 strain were added 4.0 ml of 0.05M (pH 7.0) phosphate buffer and 1.0 ml of 10% gum arabic solution. The resultant mixture was treated with a high flex homogenizer at 15000 rpm for 4 minutes to be emulsified. The resultant was divided into 500 µl each, and then 50 U/100 µl of *Rhizopus oryzae* (lipase of Amano F-AP15) was added thereto, and the mixtures were shaken at 37° C. After certain period of time, 1.0 ml of ether was added to stop the reaction, and lipid mixture was extracted with ether. To this was added TMS diazomethane (Tokyo Kasei), and esterification reaction was carried out at room temperature for 2 hours. Finally, acetic acid was added to stop the reaction. This reaction solution was analyzed by gas chromatography (Shimazu GC-2010, DB-17 capillary column). The fatty acid methyl ester which was released on gas chromatograph was detected. Table 1 shows the fatty acid composition of the extracted lipid. C16 component and C22 component occupy 90% or more of fat and oil. Further, FIG. 2 shows the ratio of C16 (palmitic acid) and docosahexaenoic acid in the free fatty acids from the initial stage of the reaction to 2 hours later.

TABLE 1

Fatty acid composition of the fat and oil extracted from LFF1 strain

| Fatty acids | composition ratio |
| --- | --- |
| pentadecane acid (C15:0) | 2.79 |
| palmitic acid (C16:0) | 24.67 |
| eicosapentaenoic acid (C20:5) | 2.64 |
| docosapentaenoic acid (C22:5) | 7.63 |
| docosahexaenoic acid (C22:6) | 62.27 |
| Total | 100.00 |

In the initial stage of the reaction, the release of C16 is very large, and as a result, the ratio of C22 component which remains in fat and oil is increased. For example, the hydrolysis ratio reaches 32.5% in the reaction of 60 minutes, where C16 component which remains as lipid (glyceride) is decreased from 24% to 10% and DHA component is increased from 62% to 84%.

To 10 g of Labyrinthulea oil extract which is a total fat and oil produced and extracted in Example 2 were added 100 ml of 0.05M (pH 7.0) phosphate buffer and 20 ml of 10% gum arabic solution. The resultant mixture was treated with a high flex homogenizer at 15000 rpm for 4 minutes to be emulsified. 2000 U of *Rhizopus oryzae* (lipase of Amano F-AP15) was added thereto, and the mixtures were shaken at 37° C. for 60 minutes. 400 ml of ethanol was added, and the mixture was cooled. Then, insoluble matters were filtered off and ethanol was concentrated. Thereby, 5.7 g of lipid having DHA content of 79% was obtained.

Example 5

Production of Fat and Oil Using the LFF1 Strain (pH Condition)

The LFF1 strain was cultured using a jar fermenter under the same conditions as in Example 2 to produce fat and oil. The culturing (40 hours, agitation culture with aeration at 500 rpm) was carried out while pH was adjusted to be 4.5, 7.5 or 8.0. The composition of the produced fat and oil was analyzed by gas chromatography as in Example 2.

Figure 3:
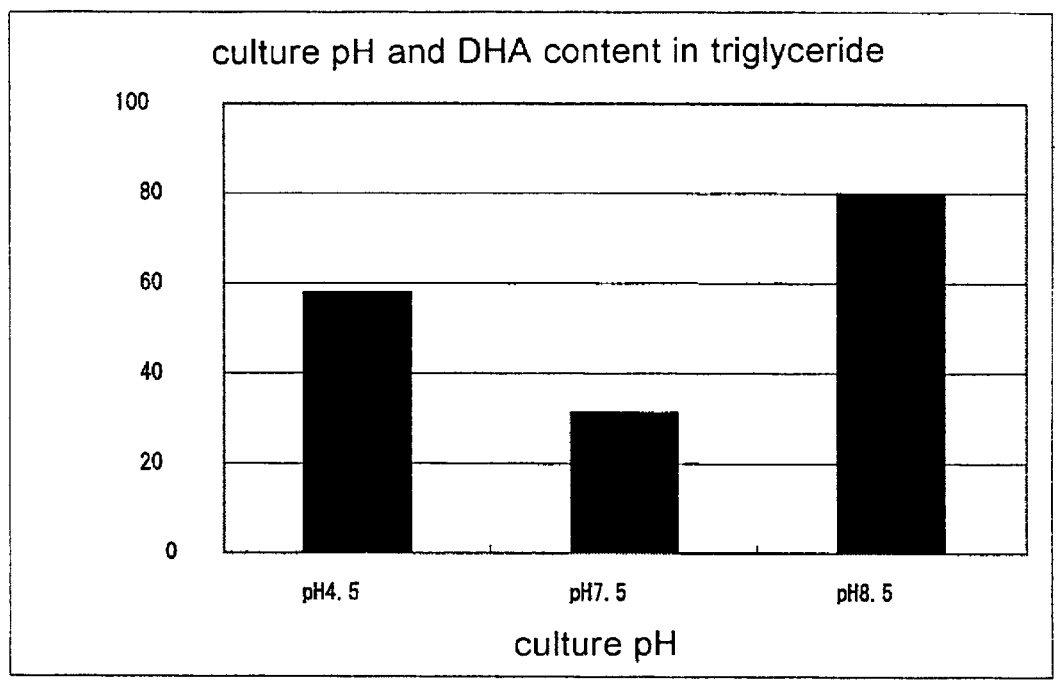
FIG. 3 is a graph showing a relationship of pH at culturing with DHA content in triglyceride.

The results of the culturing are shown in FIG. 3. The DHA component in the triglycerides produced shows characteristic tendency. Namely, DHA component is around 40% when culturing was carried out at pH 7.5, but DHA component becomes a high content of 80% or more, when culturing was carried out at pH 8.5. The DHA yield at pH 8.5 was 0.8 g/L culture.

Example 6

Production of Fat and Oil Using the LFF1 Strain (Setting of the Amount of the Seed Strain)

The LFF1 strain was cultured using a jar fermenter under the following conditions to produce fat and oil. The composition of the produced fat and oil was analyzed by gas chromatography.

(1) Culture Conditions:
  use of a 3-liter fermenter;
  amount of culture: 1.5 liters of culture; and
  composition of medium:
  15% glucose;
  3.3% yeast extract;
  50% synthetic seawater;
  0.1% defoaming agent;
  0.2% ammonium acetate; and
  0.2% monobasic potassium phosphate.

The LFF1 strain for subculture was streaked onto agarose medium and then subjected to standing culture at 28° C. for 4 days. The appeared colonies were then refrigerated.
  Agarose medium:
  3% glucose;
  1% yeast extract;
  50% synthetic seawater;
  0.2% ammonium acetate;
  0.2% monobasic potassium phosphate; and
  1.5% agarose The aforementioned colonies were collected and then subjected to preculture while stirring in 2000 ml of medium at 28° C. under aerobic conditions for 24 hours. 1 liter of a fermenter medium was inoculated with 135 g of the seed starain. Agitation culture was conducted for 45 hours with aeration at 500 rpm. After the strains were collected at 1,500 G for 30 minutes, the wet weight was measured. After being frozen at −40° C., lyophilization was carried out overnight, and the dry weight was measured.

Conditions for Disruption and Extraction

Strains were extracted by adding a mixture of chloroform and methanol with a chloroform-to-methanol ratio of 2:1 in an amount 10 times greater than that of the strain (based on a wet weight) and also adding glass beads in an amount equivalent to that of the strain (based on a wet weight), and then stirring the resultant mixture under water cooling in a high-performance agitator. The disrupted strains were separated by filtration, extracted and washed twice with an equivalent amount of saturated saline solution, and then dried over sodium sulfate. The solvent was removed using an evaporator, and the weight of roughly purified oil was measured.

Preparation of Samples for Gas Chromatography

The oil was dissolved with the aid of chloroform, a mixture of 10% KOH (aq) and ethanol in equal proportions was added, and the mixture was hydrolyzed at 95° C. for 2 hours. The product was neutralized with 2N HCl and then extracted with ether. TMS diazomethane was added thereto, the mixture was subjected to esterification at room temperature for 2 hours, and acetic acid was finally added thereto to terminate the reaction. This reaction solution was analyzed by gas chromatography.

Conditions for Gas Chromatography
  Column: DB-17 (0.25 mm×30 m)
  Carrier gas: He inlet pressure of 250 kPa
  Column temperature: 100° C. to 250° C. (rate of temperature increase: 10° C./minute)
  Detection: FID As a result of the culture, the DHA content in the triglycerides produced was 32%, and the production amount of fat and oil was 52 g/liter of culture. The yield of DHA was 16.6 g/liter of culture.

Example 7

Production of Fat and Oil Using the LFF1 Strain (Using 2 Types of Medium)

The LFF1 strain was cultured using a jar fermenter under the following conditions to produce fat and oil. The composition of the produced fat and oil was analyzed by gas chromatography.

(1) Culture Conditions:
  use of a 3-liter fermenter;
  amount of culture: 1.5 liters of culture; and
  Composition of Medium 1
  6% glucose;
  3.3% yeast extract;
  50% synthetic seawater;
  0.1% defoaming agent;
  0.2% ammonium acetate; and
  0.2% monobasic potassium phosphate.
  Composition of Medium 2
  15% glucose;
  3.3% yeast extract;
  50% synthetic seawater;
  0.1% defoaming agent;
  0.2% ammonium acetate; and
  0.2% monobasic potassium phosphate.

The LFF1 strain for subculture was streaked onto agarose medium and then subjected to standing culture at 28° C. for 4 days. The appeared colonies were then refrigerated.
  Agarose medium:
  3% glucose;
  1% yeast extract;
  50% synthetic seawater;
  0.2% ammonium acetate;
  0.2% monobasic potassium phosphate; and
  1.5% agarose The aforementioned colonies were collected and then subjected to preculture while stirring in 400 ml of medium at 28° C. under aerobic conditions for 24 hours. Agitation culture was conducted for 24 hours with aeration at 500 rpm using the composition of medium 1 in a fermenter. Thereafter, this medium 1 was removed, and culture was conducted for 45 hours using the composition of medium 2 in a fermenter. After the strains were collected at 1,500 G for 30 minutes, the wet weight was measured. After being frozen at −40° C., lyophilization was carried out overnight, and the dry weight was measured.

Conditions for Disruption and Extraction

Strains were extracted by adding a mixture of chloroform and methanol with a chloroform-to-methanol ratio of 2:1 in an amount 10 times greater than that of the strain (based on a wet weight) and also adding glass beads in an amount equivalent to that of the strain (based on a wet weight), and then stirring the resultant mixture under water cooling in a high-performance agitator. The disrupted strains were separated by filtration, extracted and washed twice with an equivalent amount of saturated saline solution, and then dried over sodium sulfate. The solvent was removed using an evaporator, and the weight of roughly purified oil was measured.

Preparation of Samples for Gas Chromatography

The oil was dissolved with the aid of chloroform, a mixture of 10% KOH (aq) and ethanol in equal proportions was added, and the mixture was hydrolyzed at 95° C. for 2 hours. The product was neutralized with 2N HCl and then extracted with ether. TMS diazomethane was added thereto, the mixture was subjected to esterification at room temperature for 2 hours, and acetic acid was finally added thereto to terminate the reaction. This reaction solution was analyzed by gas chromatography.

Conditions for Gas Chromatography

Column: DB-17 (0.25 mm×30 m)
Carrier gas: He inlet pressure of 250 kPa
Column temperature: 100° C. to 250° C. (rate of temperature increase: 10° C./minute)
Detection: FID As a result of the culture, the DHA content in the triglycerides produced was 34%, and the production amount of fat and oil was 45 g/liter of culture. The yield of DHA was 15.3 g/liter of culture.

INDUSTRIAL APPLICABILITY

Docosahexaenoic acid (DHA) and behenic acid can be stably provided in a highly pure form at a low cost by producing fat and oil through culturing the *Thraustochytrium* strain which has an ability of producing the docosahexaenoic acid according to the present invention. Thus, by using the *Thraustochytrium* strain of the present invention, fat and oil containing a large amount of docosahexaenoic acid which is useful in the fields of, for example, photographic materials, foods and drinks, cosmetics, or medicines, can be efficiently produced at a high yield.

The invention claimed is:

1. A method for producing docosahexaenoic acid-containing fat and oil, which comprises culturing *Thraustochytrium* strain, deposited as IPOD Accession NO. FERM BP-08568, which has an ability of producing docosahexaenoic acid, or a strain having all of the identifying characteristics of the strain FERM BP-08568 in a medium, and collecting the docosahexaenoic acid-containing fat and oil from the culture product.

2. The method for producing docosahexaenoic acid-containing fat and oil according to claim 1, wherein pH at culturing is 8.0 to 9.0.

3. The method for producing docosahexaenoic acid-containing fat and oil according to claim 1, wherein the amount of strain to be inoculated at culturing is 80 g or more per liter of culture medium.

4. The method for producing docosahexaenoic acid-containing fat and oil according to claim 3, wherein the amount of strain to be inoculated at culturing is 100 g or more per liter of culture medium.

5. The method for producing docosahexaenoic acid-containing fat and oil according to claim 1, wherein the strain is cultured in a medium having a carbon source concentration of 4% to 7%, and then is subsequently cultured in a medium having a carbon source concentration of 13% to 20%.

* * * * *